(12) United States Patent
Johnson

(10) Patent No.: US 10,362,805 B2
(45) Date of Patent: Jul. 30, 2019

(54) WICKLESS CARTOMIZER

(71) Applicant: Intrepid Brands, LLC, Louisville, KY (US)

(72) Inventor: David Michael Johnson, Owensboro, KY (US)

(73) Assignee: Intrepid Brands, LLC, Louisville, KY (US)

(*) Notice: Subject to any disclaimer, the term of this patent is extended or adjusted under 35 U.S.C. 154(b) by 144 days.

(21) Appl. No.: 15/673,970

(22) Filed: Aug. 10, 2017

(65) Prior Publication Data

US 2018/0042307 A1 Feb. 15, 2018

Related U.S. Application Data

(60) Provisional application No. 62/374,164, filed on Aug. 12, 2016.

(51) Int. Cl.
*A24F 47/00* (2006.01)
*H05B 3/44* (2006.01)
*A61M 15/06* (2006.01)
*A61M 11/04* (2006.01)

(52) U.S. Cl.
CPC ......... *A24F 47/008* (2013.01); *A61M 11/042* (2014.02); *A61M 15/06* (2013.01); *H05B 3/44* (2013.01); *A61M 2205/3368* (2013.01); *A61M 2205/3653* (2013.01); *A61M 2205/8206* (2013.01)

(58) Field of Classification Search
CPC .................................................... A24F 47/008
See application file for complete search history.

(56) References Cited

U.S. PATENT DOCUMENTS

| 7,832,410 | B2* | 11/2010 | Hon | A24F 47/008 131/273 |
| 8,365,742 | B2* | 2/2013 | Hon | A24F 47/008 131/273 |
| 9,271,529 | B2* | 3/2016 | Alima | A24F 47/008 |
| 9,999,250 | B2* | 6/2018 | Minskoff | A61M 15/06 |
| 9,999,253 | B2* | 6/2018 | Li | F16K 15/14 |
| 2015/0282530 | A1* | 10/2015 | Johnson | A24F 47/008 392/387 |
| 2016/0227837 | A1* | 8/2016 | Hammel | A24F 47/008 |
| 2017/0347714 | A1* | 12/2017 | Metz | A24F 47/008 |
| 2018/0042307 | A1* | 2/2018 | Johnson | A24F 47/008 |

* cited by examiner

*Primary Examiner* — James Harvey
(74) *Attorney, Agent, or Firm* — Frost Brown Todd LLC

(57) ABSTRACT

A wickless cartomizer includes an outer shell surrounding an inner shell in a spaced configuration to form chamber for holding vaporizable material between the outer and inner shell. The inner shell includes a channel having an opening at the bottom portion of the outer wall to allow the vaporizable material in the chamber to flow into the channel such that the vaporizable material within the channel is substantially level with the vaporizable material in the chamber. The inner wall of the channel includes a heater to heat the vaporizable material stored within the channel along the length of the inner wall to provide a more even temperature distribution through the vaporizable material. As the vaporizable material heats and becomes vaporized, the vapor rises and passes through a vapor exit opening in a top portion of the inner wall of the channel.

20 Claims, 11 Drawing Sheets

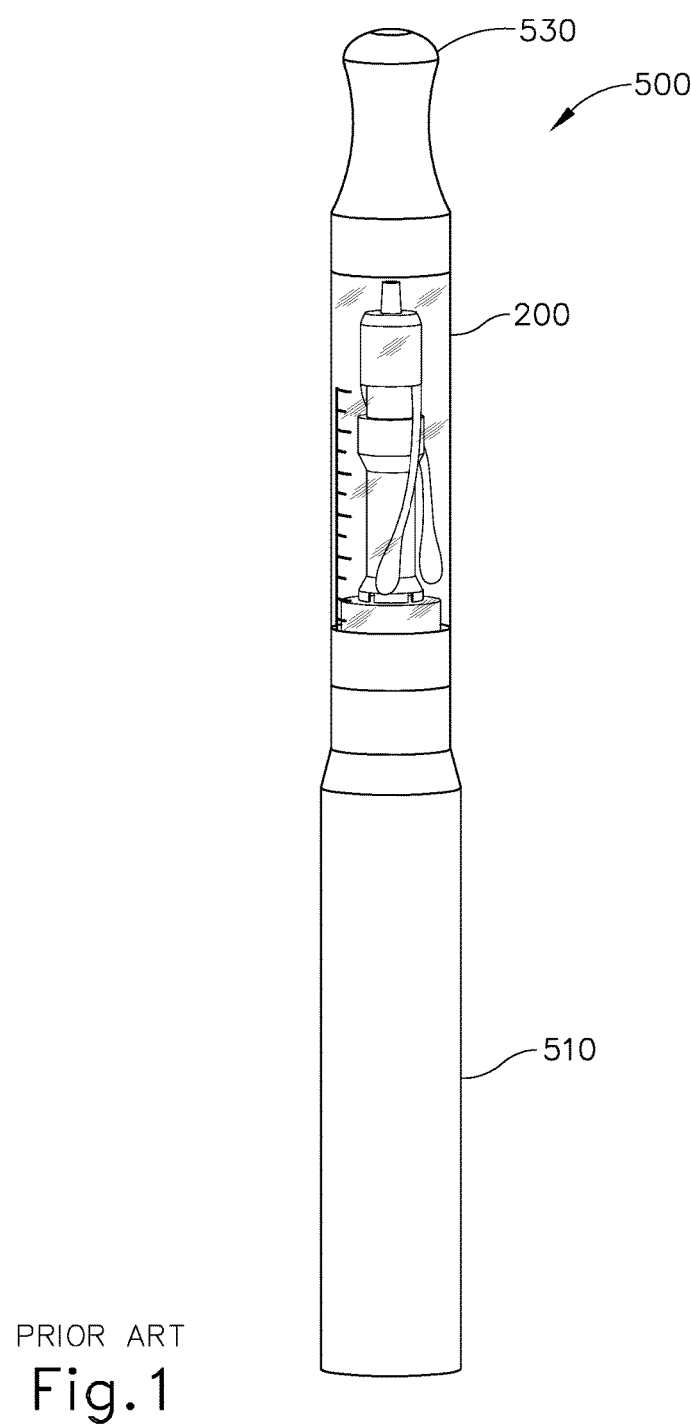
PRIOR ART
Fig.1

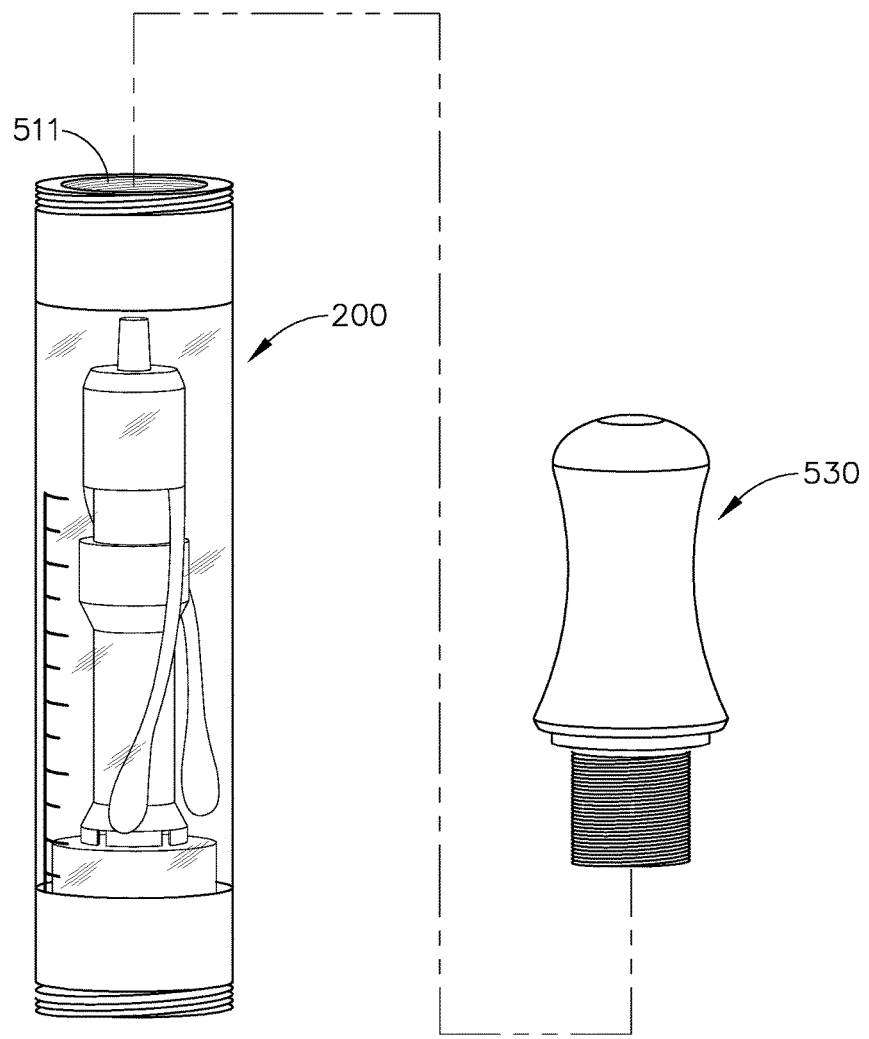
PRIOR ART
Fig.2A

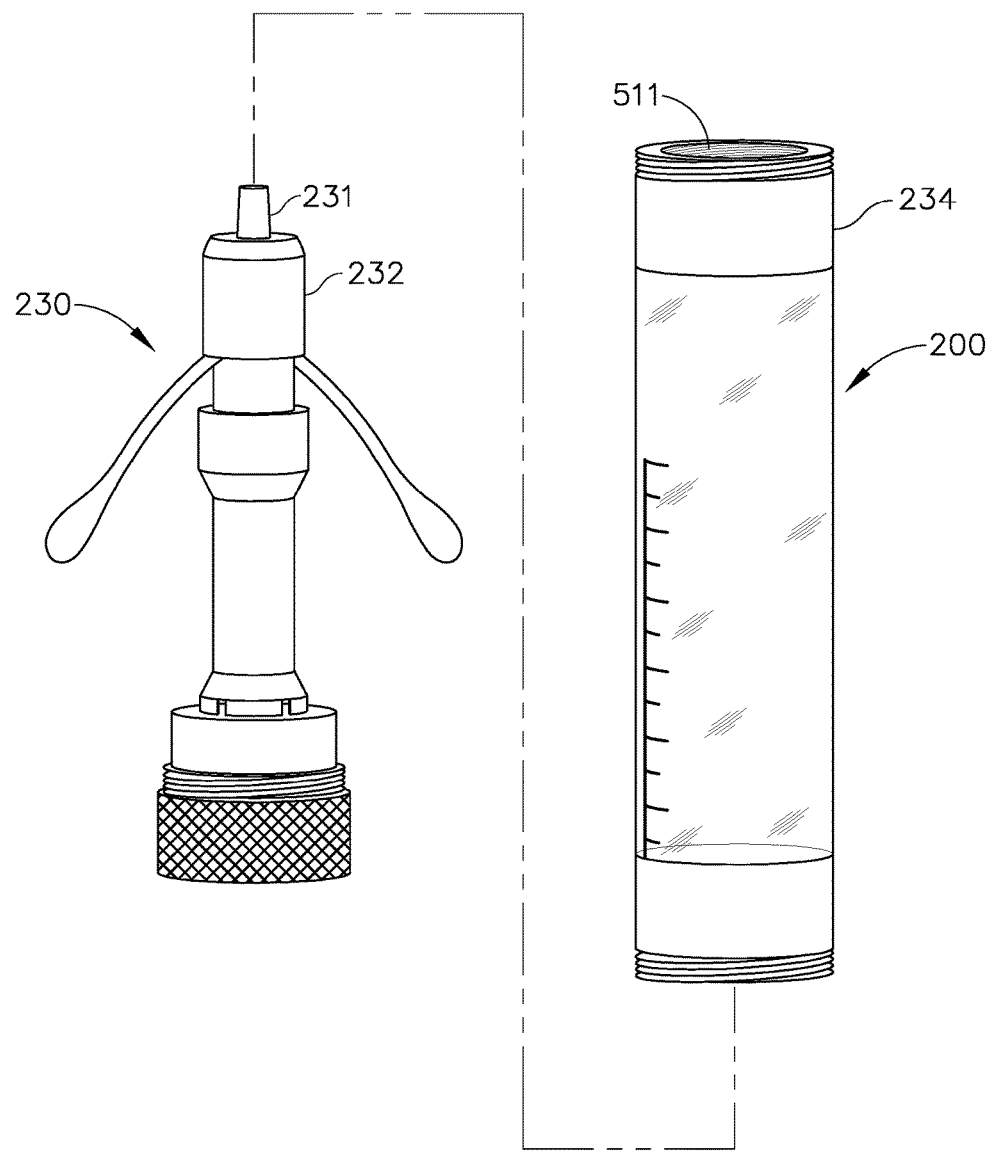
PRIOR ART
Fig.2B

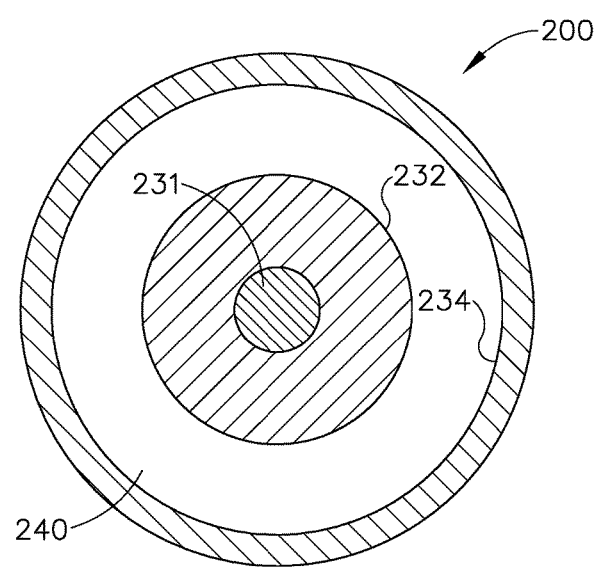
PRIOR ART
Fig.2C

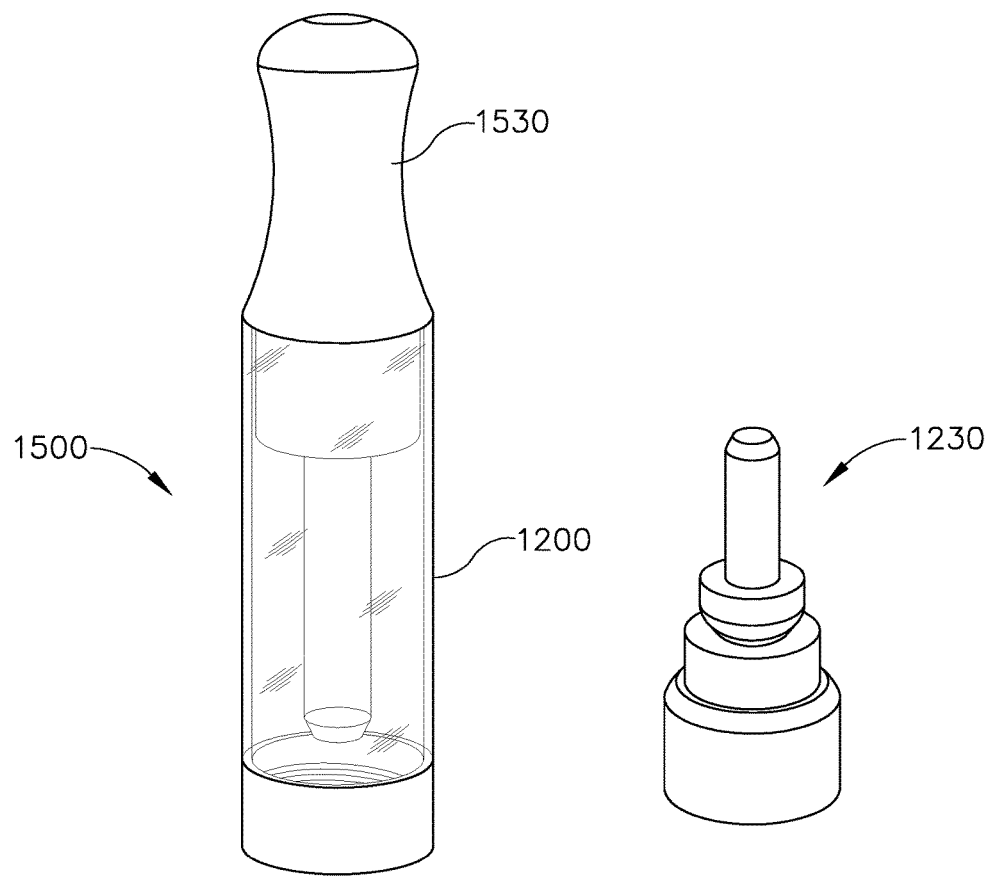
PRIOR ART
Fig.3A

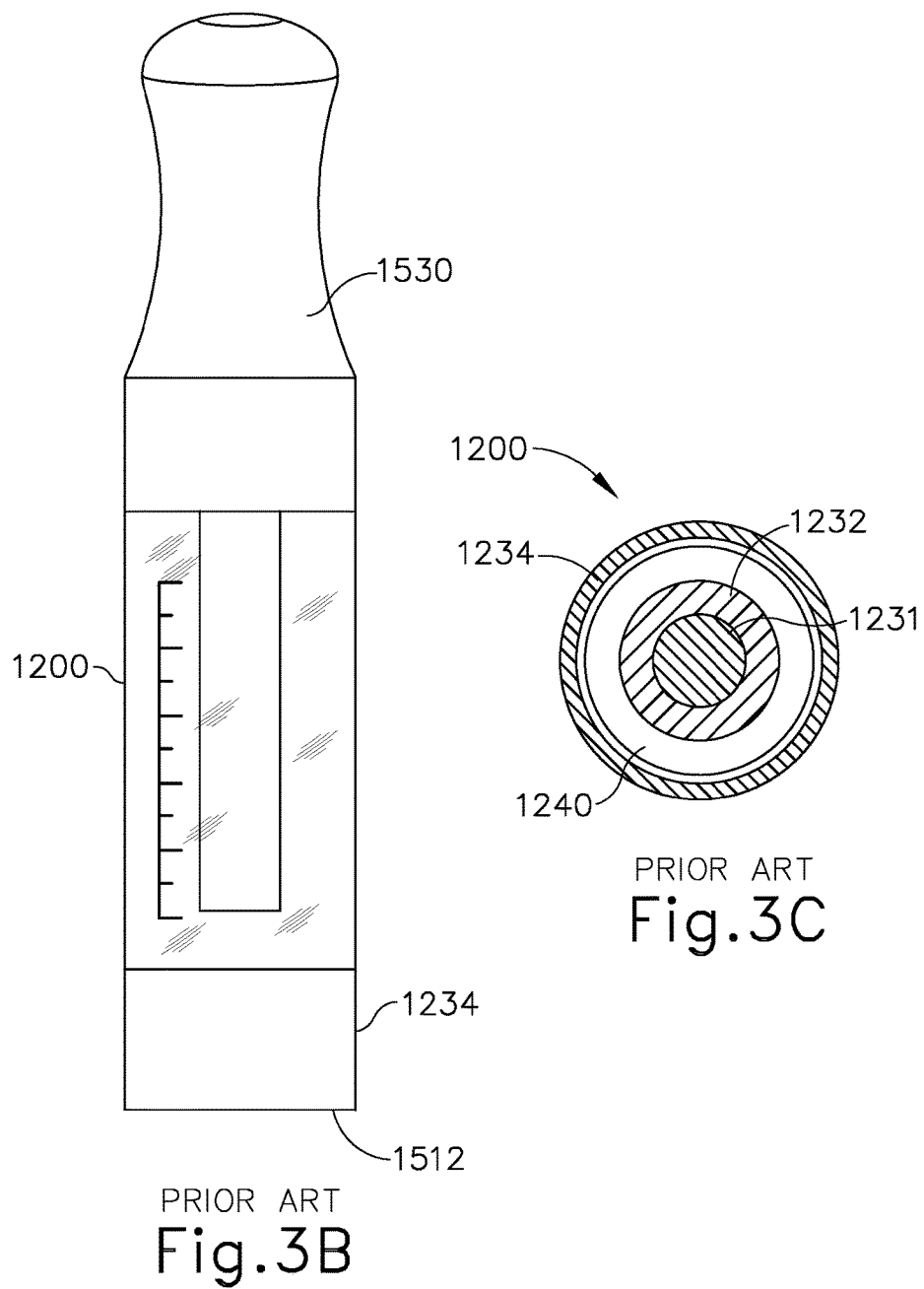
PRIOR ART
Fig.3B
PRIOR ART
Fig.3C

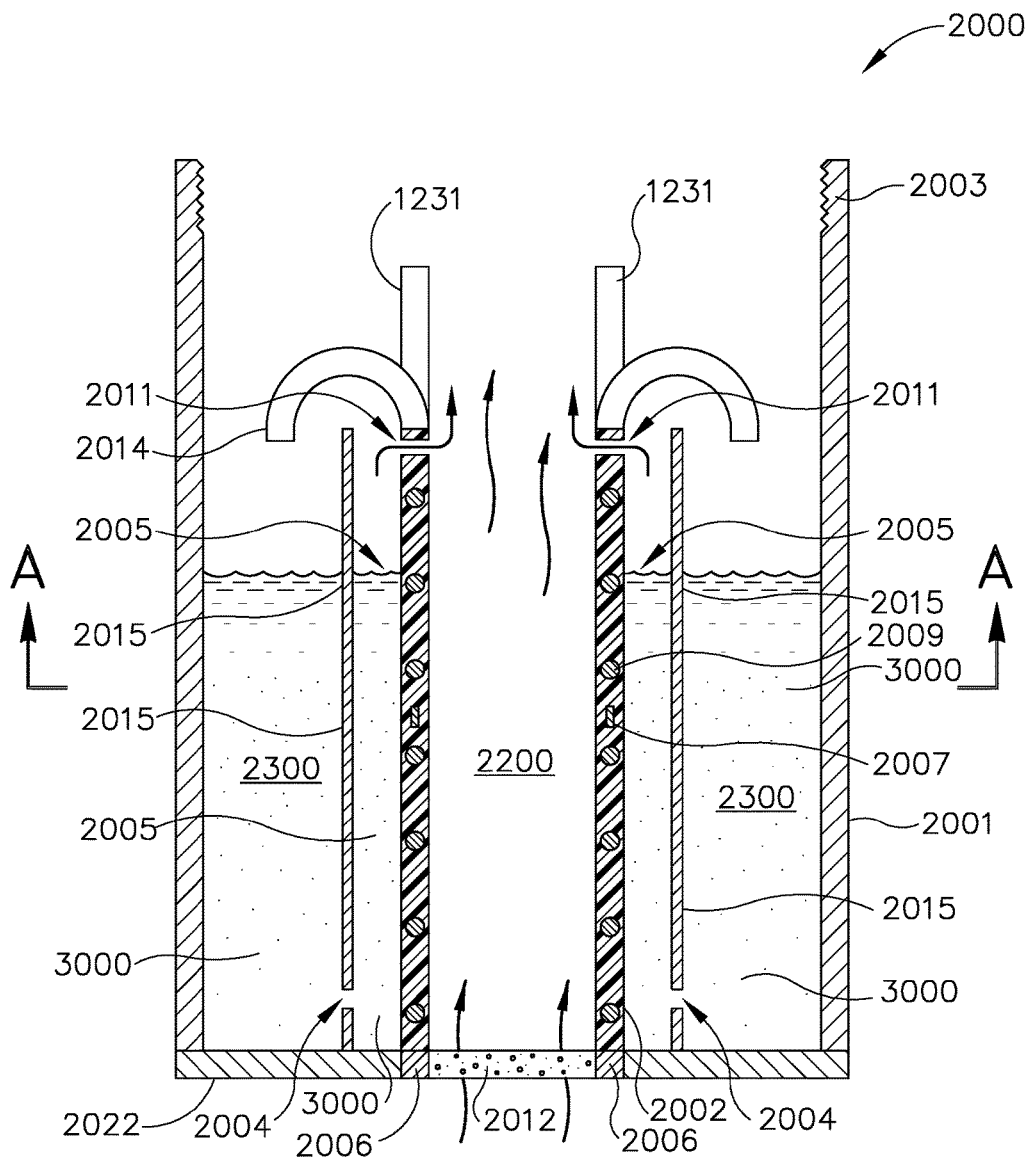
Fig.4

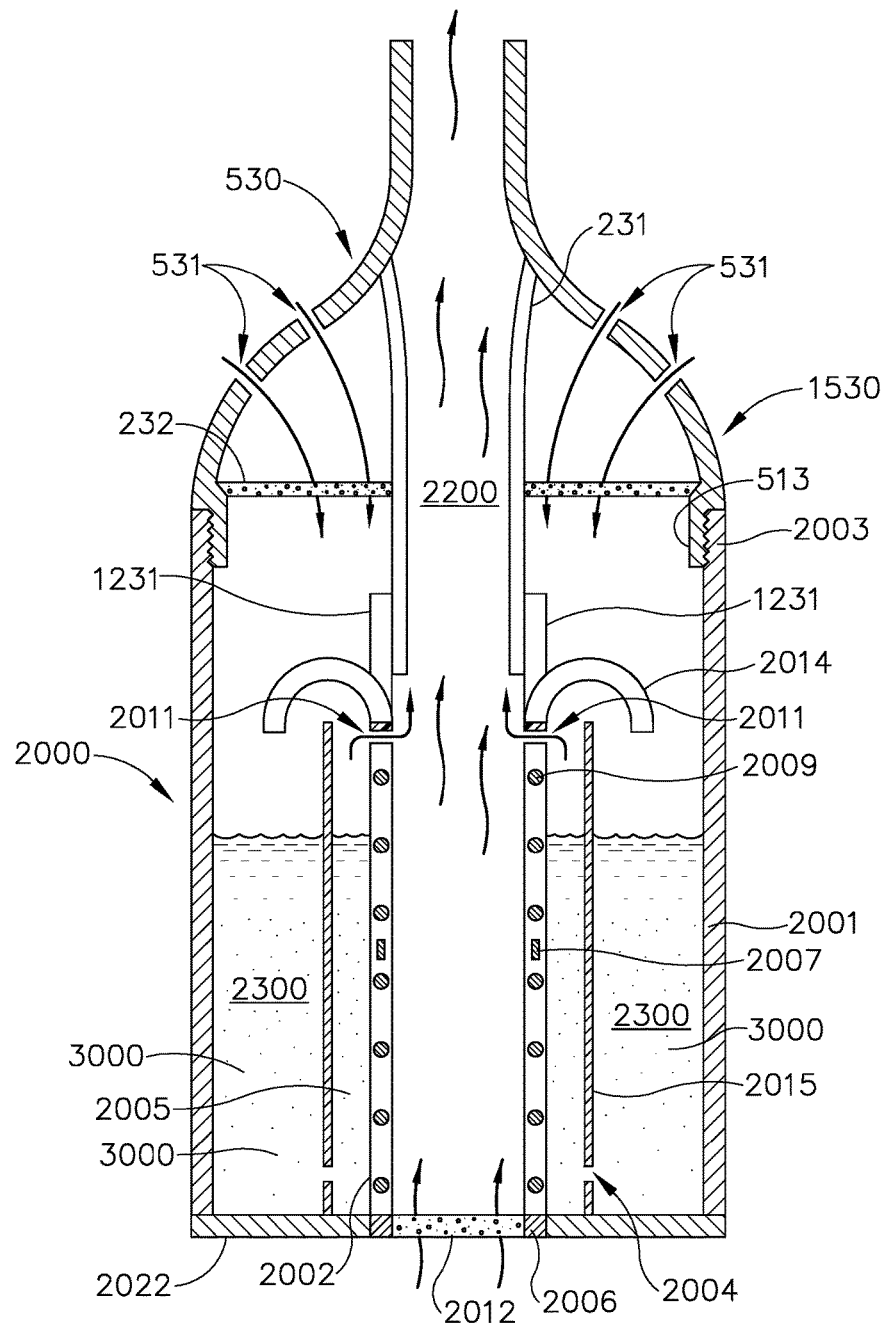
Fig.5

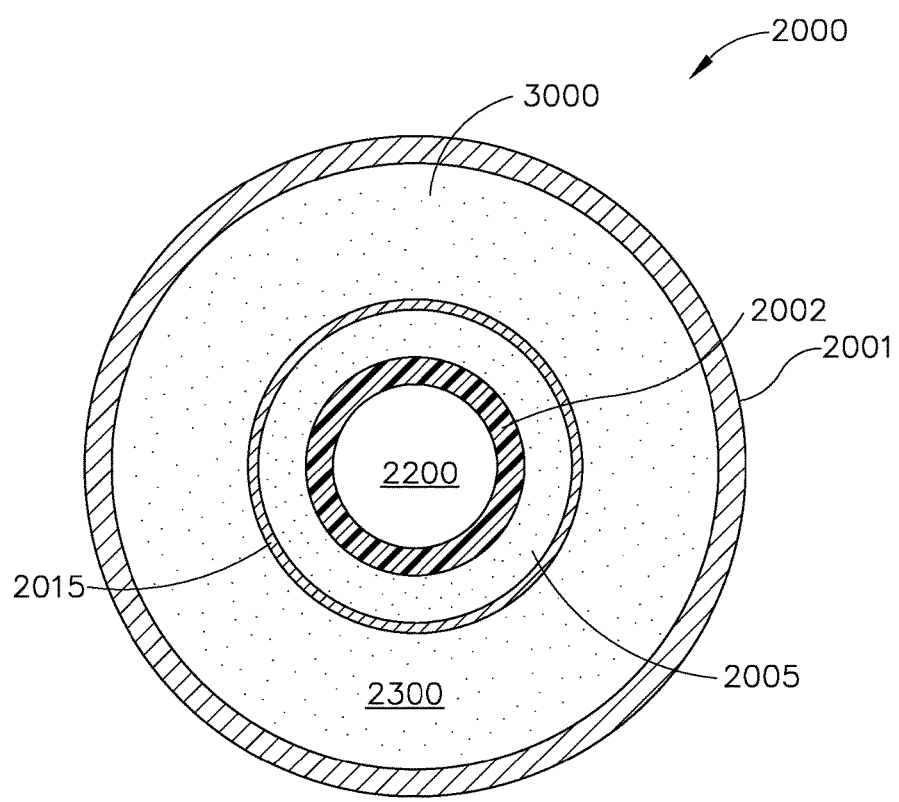
Fig.6

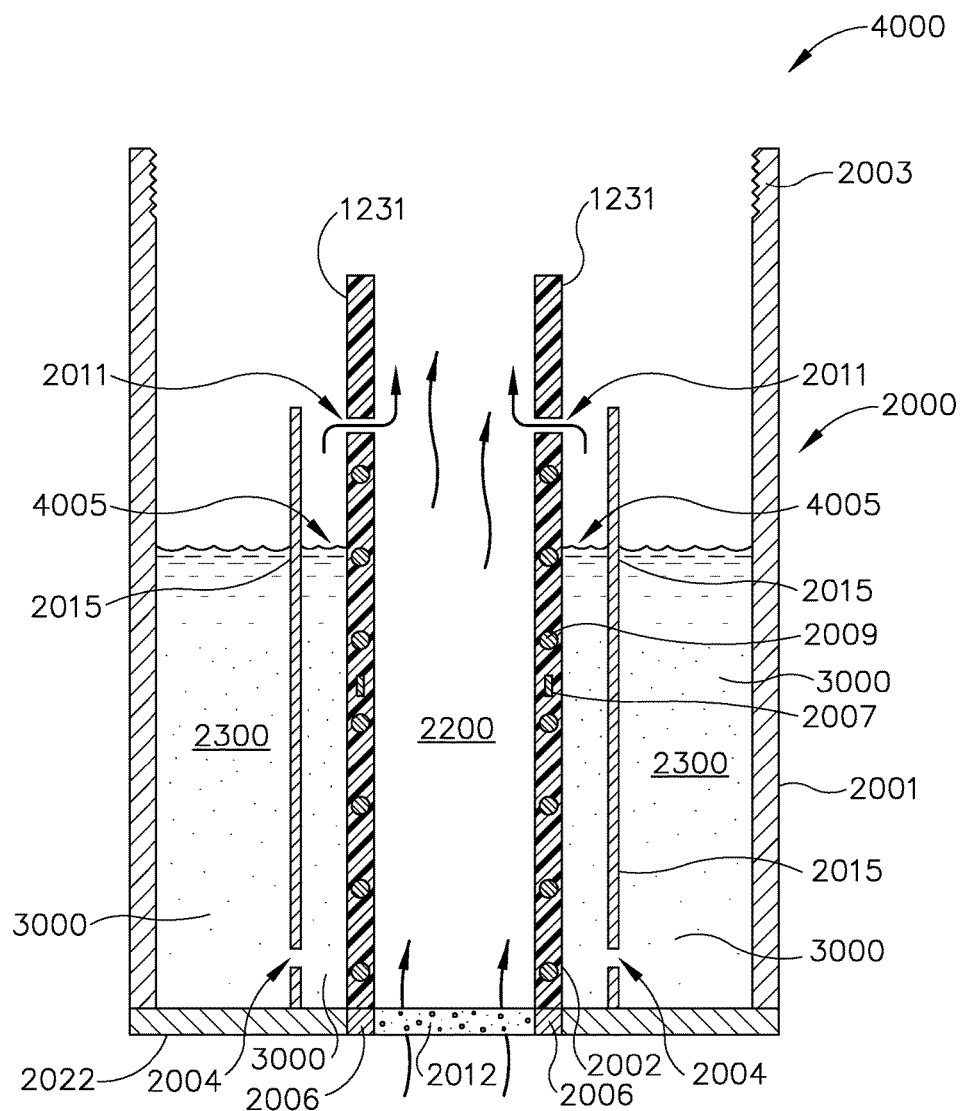
Fig.7

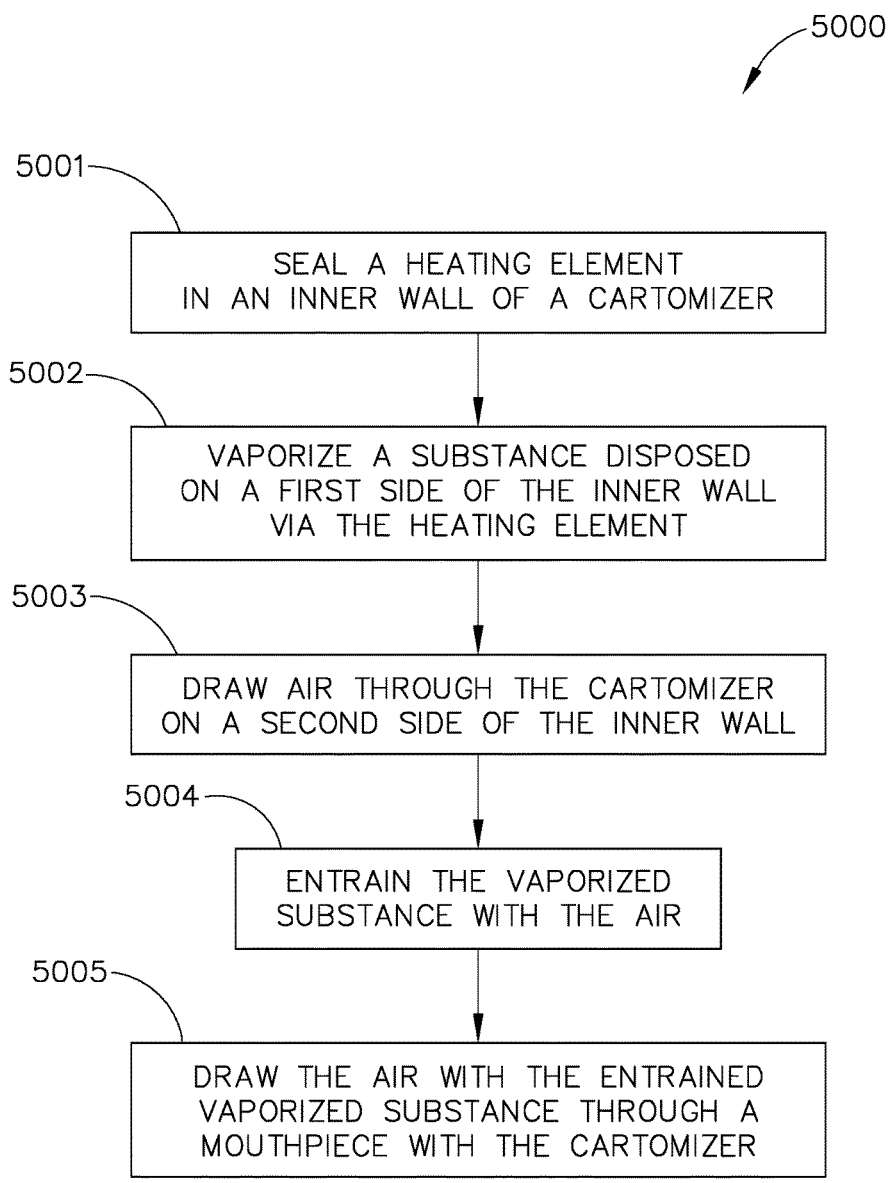
Fig.8

WICKLESS CARTOMIZER

PRIORITY

This application claims priority to U.S. Provisional Patent Application Ser. No. 62/374,164, filed on Aug. 12, 2016, and entitled, "Wickless Cartomizer," the disclosure of which is incorporated herein.

TECHNICAL FIELD

The disclosure is directed to wickless cartomizers. The wickless cartomizers may be used as part of an electronic vaporization device, such as an e-cigarette or personal vaporizer, to vaporize certain materials.

BACKGROUND

Vaporization provides an alternative to combustion for the delivery and consumption of various substances including, but not limited to liquids, i.e., "E-liquids," waxes, gels, herbal materials and combinations thereof (singularly herein, "a vaporizable substance," collectively herein, "vaporizable substances"). Non-limiting examples of components of vaporizable substances include: glycerin, propylene glycol, flavorings, nicotine, medicaments and combinations thereof. Vaporization may be accomplished using electronic vaporization devices, including, but not limited to, electronic cigarettes, electronic cigars, electronic pipes and electronic vaporizers (singularly "EVD," collectively, "EVDs").

Oftentimes, a vaporizable substance is placed into a chamber, which either contains, or interfaces with, a heat source of an EVD. The chamber which contains the vaporizable substance may take a variety of forms, depending upon the configuration of the EVD. Some chambers are referred to in the art as "cartomizers." "Clearomizers," are a subset of cartomizers that are see-through, i.e., they comprise plastic or glass for example.

Typically, cartomizers contain a heating source, such as an atomizer. Atomizers comprise an absorbent material or chamber containing a vaporizable substance. The absorbent material or chamber is fluidly connected to a porous component such as a wick, which in turn acts to transport the vaporizable substance, i.e., the E-liquid, gel or melted wax, to a heating source that heats it and releases vapor. Oftentimes, the heating source comprises a heating wire wound around the porous component. Cartomizers may further comprise a vapor chimney through which the resulting vapor passes to be delivered to the consumer, such as via a mouthpiece. Exemplary cartomizers and e-cigarettes comprising the same, include those described in U.S. Pat. Nos. 8,365,742 (to Lik Hon) and 7,832,410B2 (to Lik Hon).

Some personal vaporizers such as those disclosed in U.S. Pat. No. 9,271,529 (to Yariv Alima), comprise cartomizers into which a vaporizable substance is dispensed and then heated via a metal coil that is in direct contact with the vaporizable substance.

The aforementioned cartomizers and the EVDs comprising them may be characterized by a number of disadvantages including, but not limited to, any one or more of the following: exposure of the vaporizable substance to certain metals that may result in a tainted vapor flavor; being useful only to vaporize e-liquids or waxes or gels, and not of use to vaporize all three; undesired contamination components of the cartomizer, EVD or EVD components (e.g., the EVD mouthpiece), when the EVD is inverted (such as being placed in a consumer's pocket); being difficult to clean between uses; being difficult to fill due to the presence of coils, wicks and other components; and limiting flow of vaporizable material based upon the physical characteristics of the porous material, i.e., wick, that delivers the vaporizable material to the heat source where it is to be vaporized.

For these and other reasons, there remains a need for an improved cartomizer that eliminates these and other problems.

SUMMARY

The unique solution that addresses the aforementioned problems is a wickless cartomizer as shown and described herein. The wickless cartomizer may eliminate the need to use a wick or porous material to transfer the vaporizable material to be vaporized. By eliminating these components, loss of the vaporizable material is reduced, thereby increasing the efficiency of the EVD. The wickless cartomizer may eliminate exposure of the vaporizable material to metal, e.g., a heating coil, and prevent tainting the taste of the resulting vapor and/or metallic contamination of the vapor. The wickless cartomizer may facilitate cleaning of the cartomizer between uses by eliminating components such as wicks and metal coils. The mouthpiece of the wickless cartomizer can be removable to make filling and/or cleaning the cartomizer easier. Moreover, the wickless cartomizer may include a semi-permeable seal to prevent leaking of the vaporizable substance from the cartomizer if it, or the EVD in which it is incorporated, is inverted, while still allowing for vapor to pass through the semi-permeable seal and be delivered to the consumer.

BRIEF DESCRIPTION OF THE DRAWINGS

FIG. 1 is a schematic diagram of a typical Electronic Vaporization Device.

FIGS. 2a, 2b and 2c are schematic diagrams of a top-filled cartomizer, or a top-filled cartomizer, of use in the EVD shown in FIG. 1.

FIGS. 3a, 3b and 3c are schematic diagrams of a typical bottom-fed chamber, or a bottom-fed chamber and mouthpiece, of use in the EVD shown in FIG. 1.

FIG. 4 is a cross-sectional view of an exemplary wickless cartomizer.

FIG. 5 is a cross-sectional view of the wickless cartomizer of FIG. 4 coupled with a mouthpiece.

FIG. 6 is a cross-sectional view of the wickless cartomizer of FIG. 4 taken along section line A-A.

FIG. 7 is a cross-sectional view of another exemplary wickless cartomizer.

FIG. 8 is a flowchart depicting an exemplary method of vaporizing a substance in a wickless cartomizer.

DETAILED DESCRIPTION

The terms "chamber," "liquid chamber," "tank," "liquidmizer," "cartomizer" and "clearomizer," are used interchangeably herein to mean a reservoir that contains vaporizable substance to be vaporized by an EVD. The chamber may be filled with a vaporizable substance through its open top, i.e., be a "top-filled chamber," or it may be filled with a vaporizable substance through its open bottom, i.e., a "bottom-filled chamber."

"Electronic vaporization device" or "EVD" as used herein, means any electronic device which vaporizes liquid for consumption including, but not limited to, via inhalation, by a consumer. EVDs include, but are not limited to: electronic cigarettes; electronic cigars; and electronic vaporizers.

The elements or features of the various embodiments are described in detail hereinafter. Any reference to a singular characteristic or limitation of the present disclosure shall include the corresponding plural characteristics or limitations, and vice versa, unless otherwise specified or clearly implied to the contrary by the context in which the reference is made.

The apparatuses and methods described herein may comprise, consist of, or consist essentially of the elements and features of the disclosure described herein, as well as any additional or optional components, or features described herein or otherwise useful in relation to the apparatuses and methods.

All documents (patents, patent applications and other publications) cited in this application are incorporated herein by reference in their entirety.

FIG. 1 shows a typical EVD 500. The EVD 500 comprises a battery compartment 510 that is removeably attached to a chamber 200. The chamber 200 is in turn removeably attached to a mouthpiece 530.

Referencing FIG. 2a, the chamber 200 and mouthpiece 530 are shown after they have been detached from the battery compartment 510 (not shown) and each other. In this embodiment, the chamber 200 has an open top 511. Vaporizable material, in this instance, E-liquid, is dispensed into the chamber 200 through the open top 511, typically using an eye dropper or syringe; thus, the chamber is a top-filled chamber. The mouthpiece 530 is then reattached to the open top 511 of the chamber 200 so that the chamber 200 is sealed. The filling process may occur with or without detaching the chamber 200 from the battery compartment 510 of the EVD.

FIG. 2b shows the chamber 200 of FIG. 2a in a disassembled state. Beginning at the left of FIG. 2b, an atomizer assembly 230 is shown. Extending from the atomizer assembly 230 is a vapor chimney 231, which is surrounded in part by a sealing ring 232. When the chamber 200 is assembled, the atomizer assembly 230 and vapor chimney 231 fit into the chamber 200. The chamber 200 is capped at its open top 511 by a hollow metal ring 234 that comprises threads 513 on the outside and which serves as the attachment point of the mouthpiece (not shown) to the chamber 200.

FIG. 2c is a top plan view of the chamber 200 shown in FIG. 2b after it has been reassembled, i.e., the atomizer assembly 230 and vapor chimney 231 have been re-inserted into the chamber 200, such that the chamber contains them. Starting at the edges of the chamber 200 and moving inward, FIG. 2c shows the hollow metal ring 234. Moving further inward, the sealing ring 232 and top of the vapor chimney 231 are shown. As can be seen in FIG. 2c, there is a narrow gap 240 between the sealing ring 232 and the hollow metal ring 234; it is through the narrow gap 240 that E-liquid is dispensed to fill the chamber 200. Since the gap 240 is narrow, it can be very difficult to fill the chamber 200 without spilling the E-liquid down the outside of the chamber 200 and contaminating the outside of the chamber 200, and/or the other portions of the EVD. Moreover, if the narrow gap 240 is missed or filled too quickly, E-liquid may undesirably be dispensed into the top 233 of the vapor chimney 231, which may in turn result in malfunction of the EVD.

FIG. 3a shows an alternative embodiment of a chamber 1200 that is similar to the chamber 200, except that rather than detach the mouthpiece 530 from the top 511 of the chamber 200 to fill the chamber with E-liquid as described above, the atomizer assembly 1230 is removed from the bottom 1512 of the chamber 1200, as shown in FIG. 3b.

FIG. 3b shows the chamber 1200 of FIG. 3a, after the atomizer assembly 1230 has been removed. FIG. 3c shows a bottom plan view of the chamber 1200 of FIG. 3b. Starting at the edges of the chamber 1200 and moving inward, FIG. 3c shows a hollow metal ring 1234 that is threaded on the inside and which serves as the attachment point of the atomizer assembly 1230. Moving further inward, the bottom 1232 of the vapor chimney 1231 is shown. As can be seen in FIG. 3c, there is a narrow gap 1240 between the bottom 1232 of the vapor chimney 1231 and the hollow metal ring 1234. It is through the narrow gap 1240 that E-liquid is dispensed to fill the chamber 1200. Thus, the chamber 1200 depicted in FIG. 3b is a bottom-filled chamber. Since the gap 1240 is narrow, it can be very difficult to fill the chamber 1200 without spilling the E-liquid down the outside of the chamber 1200 and contaminating the outside of the chamber 1200, and/or the other portions of the EVD (e.g., the mouthpiece). Moreover, if the narrow gap 1240 is missed or filled too quickly, E-liquid may undesirably be dispensed into the bottom 1232 of the vapor chimney 1231. This can be problematic, because E-liquid may then flow from the vapor chimney 1231 into the atomizer assembly 1230 after the chamber 1200 has been reassembled, thereby contaminating the atomizer assembly and possibly causing it to malfunction.

FIGS. 4-6 show an exemplary wickless cartomizer 2000. Wickless cartomizer 2000 may be utilized with a typical EVD such as the EVD 500 shown in FIG. 1. In particular, the wickless cartomizer 2000 can be substituted for the chamber 200 or 1200. A wickless cartomizer 2000 may be sold as a unit 1530 together with a mouthpiece 530 as shown in FIG. 5, and/or may be sold as a component of an EVD 500 such as the one shown in FIG. 1, which further comprises a mouthpiece 530 and battery compartment 510.

Wickless cartomizer 2000 is configured to hold vaporizable material 3000. Wickless cartomizer 2000 comprises an outer shell 2001 and an inner shell 2002. The outer shell 2001 comprises a threaded portion 2003 at a top of the outer shell 2001 to removeably couple the wickless cartomizer 2000 with a mouthpiece of an EVD as shown in FIG. 5.

Wall 2015 is disposed between outer shell 2001 and inner shell 2002 of the cartomizer 2000. Liquid reservoir 2300 is formed by outer shell 2001, wall 2015 and base 2022. A Liquid channel 2005 is formed by the inner shell 2002, wall 2015 and base 2022 of the cartomizer 2000. Thus, the inner shell 2002 of the cartomizer 2000 is also the inner wall 2002 of the liquid channel 2005, and the wall 2015 of the cartomizer 2000 is also the outer wall 2015 of the channel.

The liquid channel 2005 has an opening 2004 at the bottom portion of the outer wall 2015 of the liquid channel 2005. This allows the vaporizable material 3000 in the wickless cartomizer 2000 to flow into the liquid channel 2005 from the liquid reservoir 2300 such that the vaporizable material 3000 within the liquid channel 2005 is substantially level with the vaporizable material 3000 in the liquid reservoir 2300.

The liquid channel 2005 further comprises a heating element. In the exemplary wickless cartomizer 2000 shown in FIGS. 4 and 5, heating element is a resistance heater 2009 enclosed in ceramic, or other suitable material, in the inner wall 2002 of the liquid channel 2005. The resistance heater 2009 is configured to heat the vaporizable material 3000 contained within the liquid channel 2005 along the inner wall 2002 of the channel. This provides for even temperature distribution through the vaporizable material 3000, which may in turn prevent portions of the vaporizable material 3000 from being overheated or burnt or under-heated. In the illustrated embodiment, the base of the inner shell 2002 of the cartomizer 2000 comprises an electrical connection 2006 to electrically couple the heater 2009 to a power source of an EVD, such as a battery. The inner wall 2002 of the liquid channel 2005 further comprises a thermocouple 2007 for temperature control. As the vaporizable material 3000 heats and becomes vaporized, the vapor rises and passes through a vapor exit opening 2011 in a top portion of the inner wall 2002 of the liquid channel 2005.

The inner wall 2002 of the liquid channel 2005 forms an air channel 2200. In the illustrated embodiment, the bottom of the air channel 2200 comprises a porous air flow plate 2012. This allows air to enter from the atmosphere through the air flow plate 2012 and flow upwards through the air channel 2200 when a user inhales through the mouthpiece 530. In some instances, the air flow plate 2012 acts as a filter. The vapor exiting through the vapor exit openings 2011 of the liquid channel 2005 then mixes with atmospheric air, entraining the vapor in the air. The entrained vapor flows upwardly through the mouthpiece 530. Referring to FIGS. 4 and 5, exemplary vapor flow and exemplary flow of entrained vapor is depicted by upward arrows.

A top portion of the liquid channel 2005 comprises a seal support 1231. As shown in FIG. 5, when mouthpiece 530 is attached to the wickless cartomizer 2000, the sealing ring 232 of the mouthpiece 530 is seated upon seal support 1231 to form an upper portion of the air channel 2200. The sealing ring 232 of the mouthpiece 530 extends upwardly from a top portion of the inner wall 2002 of the liquid channel 2005 and outwardly to the outer wall 2001 of the wickless cartomizer 2000. The sealing ring 232 can comprise a semi-permeable membrane that allows gas to flow through it into the wickless cartomizer 2000, but that does not allow liquids to pass through it into the mouthpiece 530. Thus, if the wickless cartomizer 2000 is tipped upside down, the sealing ring 232 will prevent the vaporizable material from spilling into the mouthpiece 530. The vapor exit opening 2011 of the liquid channel 2005 further comprises a hinged cap 2014 that is configured to close upon inversion that also prevents the vaporizable material 3000 stored within the liquid channel 2005 to flow into the mouthpiece 530. Still other configurations for the wickless cartomizer 2000 will be apparent to one with ordinary skill in the art in view of the teachings herein.

Referring to FIG. 5, mouthpiece 530 comprises vents 531. Vents 531 allow for ambient air to enter the mouthpiece 530 (shown by downward facing arrows). Without wishing to be bound by theory, it is believed that atmospheric pressure resulting from the presence of ambient air in the mouthpiece 530 keeps vaporizable material 3000 in the liquid reservoir 2300, level with vaporizable material 3000 in the liquid channel 2005.

Referring now to FIG. 7, a second exemplary embodiment of a cartomizer 4000 is shown. The cartomizer 4000 comprises components in common with the cartomizer 2000 shown in FIGS. 4-6. However, the cartomizer 4000 comprises liquid channel 4005, which does not have a cap. Instead, liquid channel 4005 has an open top. When a mouthpiece 530 is attached to the wickless cartomizer 4000, the sealing ring 232 of a mouthpiece 530 is seated upon seal support 1231 to form an upper portion of the air channel 2200, and to seal the vaporizable material 3000 in the cartomizer 4000 such that it will not leak into the mouthpiece 530 when an assembly (not shown) comprising cartomizer 4000 and mouthpiece 530 is inverted, while allowing ambient air to pass through the sealing ring 232. Still other configurations for the wickless cartomizer 4000 will be apparent to one with ordinary skill in the art in view of the teachings herein.

Referring now to FIG. 8, an exemplary method (5000) of vaporizing a substance in a wickless cartomizer (2000, 4000) is shown and described. The wickless cartomizer (2000, 4000) comprises a heating element (2009) that is sealed within an inner wall (2002) (block 5001). A substance disposed on a first side of the inner wall via the heating element to produce a vapor (block 5002). Air is drawn through the cartomizer on a second side of the inner wall (block 5003). In response to drawing air through the cartomizer, vapor is entrained with the air (block 5004). Entrained vapor is drawn through a mouthpiece coupled with the cartomizer (block 5005).

The exemplary method may further comprise drawing the vaporized substance through a vapor exit opening defined by the inner wall to entrain the vapor with the air.

The exemplary method may further comprise sensing a temperature measurement of the inner wall with a temperature sensor; and adjusting a temperature of the heating element based at least in part on the temperature measurement.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

I claim:

1. A wickless cartomizer comprising:
   (a) a base;
   (b) an outer wall extending from the base;
   (c) an inner wall extending from the base;
   (d) a vapor exit opening defined by the inner wall;
   (e) a heating element disposed in the inner wall; and
     an electrical connector disposed in the base, wherein the electrical connector is electrically coupled with the heating element.

2. The wickless cartomizer of claim 1, further comprising an air channel defined by the inner wall, wherein the air channel is in fluid communication with the exterior of the base and the vapor exit opening.

3. The wickless cartomizer of claim 2, further comprising a liquid reservoir defined by the base, outer wall and inner wall.

4. The wickless cartomizer of claim 3, further comprising a cap extending from the inner wall towards the outer wall.

5. The wickless cartomizer of claim 4, wherein the cap includes a concave surface.

6. The wickless cartomizer of claim 4, further comprising a sealing support extending from the cap.

7. The wickless cartomizer of claim 1, wherein the heating element is sealed inside the inner wall.

8. The wickless cartomizer of claim 7, wherein the inner wall comprises a ceramic material and wherein the heating element is sealed inside the ceramic material.

9. The wickless cartomizer of claim 1, further comprising a temperature sensor disposed in the inner wall, wherein the temperature sensor is electrically coupled with the electrical connector.

10. The wickless cartomizer of claim 3, further comprising a middle wall extending from the base between the inner wall and the outer wall.

11. The wickless cartomizer of claim 10, further comprising a liquid channel defined by the middle wall proximate the base, wherein the liquid channel is configured to contain a vaporizable material.

12. The wickless cartomizer of claim 11, wherein the vapor exit opening is disposed in a top portion of the inner wall.

13. The wickless cartomizer of claim 2, further comprising:
 (f) an aperture defined by the base; and
 (g) an air flow plate disposed in the aperture;
 wherein the air flow plate is porous and the air flow plate is aligned with the air channel and configured to allow air to pass from the exterior of the base to the air channel.

14. A vaporizer comprising a wickless cartomizer, the vaporizer comprising:
 (a) a mouthpiece assembly defining a mouthpiece opening;
 (b) a battery assembly comprising a battery; and
 (c) a wickless cartomizer configured to couple with the mouthpiece assembly and the battery assembly, the wickless cartomizer comprising:
  (i) a base;
  (ii) an outer wall extending from the base in a first direction;
  (iii) an inner wall extending from the base in the first direction;
  (iv) an air channel defined by the inner wall;
  (v) a liquid channel defined by the inner wall, the outer wall, and the base, wherein the channel is configured to contain a vaporizable material;
  (vii) a vapor exit opening disposed in a top portion of the inner wall, wherein the vapor exit opening is in fluid communication with the liquid channel; channel; and
  (viii) a heating element disposed in the inner wall, wherein the heating element is electrically coupled with the battery when the wickless cartomizer is coupled with the battery assembly.

15. The vaporizer of claim 14, wherein the mouthpiece assembly defines a vent opening, wherein the vent opening is in fluid communication with the liquid channel when the wickless cartomizer is coupled with the mouthpiece assembly.

16. The vaporizer of claim 15, wherein the mouthpiece assembly comprises a membrane, wherein the membrane is intermediate the vent opening and the liquid channel when the wickless cartomizer is coupled with the mouthpiece assembly.

17. The vaporizer of claim 15, wherein the mouthpiece opening is in fluid communication with the air channel when the wickless cartomizer is coupled with the mouthpiece assembly.

18. A method of vaporizing a substance using a wickless cartomizer comprising:
 (a) a base;
 (b) an outer wall extending from the base;
 (c) an inner wall extending from the base;
 (d) a vapor exit opening defined by the inner wall;
 (e) a heating element sealed within the inner wall; and
 (f) an electrical connector disposed in the base, wherein the electrical connector is electrically coupled with the heating element;
 the method comprising:
  1. heating the substance disposed on a first side of the inner wall via the heating element to produce a vapor;
  2. drawing air through the cartomizer on a second side of the inner wall;
  3. in response to drawing air through the cartomizer, entraining the vapor with the air; and
  4. drawing the entrained vapor through a mouthpiece coupled with the cartomizer.

19. The method of claim 18, further comprising drawing the vaporized substance through a vapor exit opening defined by the inner wall to entrain the vapor with the air.

20. The method of claim 19, further comprising:
 (a) sensing a temperature measurement of the inner wall with a temperature sensor; and
 (d) adjusting a temperature of the heating element based at least in part on the temperature measurement.

* * * * *